(12) United States Patent
Uto et al.

(10) Patent No.: US 7,851,753 B2
(45) Date of Patent: Dec. 14, 2010

(54) METHOD AND APPARATUS FOR REVIEWING DEFECTS

(75) Inventors: Sachio Uto, Yokohama (JP); Shunji Maeda, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 173 days.

(21) Appl. No.: 11/478,618

(22) Filed: Jul. 3, 2006

(65) Prior Publication Data

US 2007/0057184 A1 Mar. 15, 2007

(30) Foreign Application Priority Data

Sep. 9, 2005 (JP) .............................. 2005-261563

(51) Int. Cl.
*G01N 23/00* (2006.01)
(52) U.S. Cl. ...................... 250/310; 250/306; 250/307; 250/311; 356/237.1; 356/237.2; 356/237.3; 356/237.4; 356/237.5
(58) Field of Classification Search ................. 250/310, 250/311, 307, 306, 201.3; 356/237.1, 237.2, 356/237.3, 237.4, 237.5, 239.1, 239.3, 239.7, 356/239.8; 382/145, 149
See application file for complete search history.

(56) References Cited

U.S. PATENT DOCUMENTS

| 4,523,094 A * | 6/1985 | Rossow ....................... 250/311 |
| 5,208,648 A * | 5/1993 | Batchelder et al. ........ 356/237.1 |
| 6,407,373 B1 * | 6/2002 | Dotan ...................... 250/201.3 |
| 6,521,889 B1 * | 2/2003 | Ina et al. ..................... 250/306 |
| 6,661,912 B1 * | 12/2003 | Taguchi et al. .............. 382/145 |
| 7,307,254 B2 * | 12/2007 | Yamaguchi et al. ......... 250/311 |
| 2001/0019411 A1 * | 9/2001 | Nara et al. ................... 356/394 |
| 2002/0015148 A1 * | 2/2002 | Tomomatsu ............. 356/237.2 |
| 2005/0094136 A1 * | 5/2005 | Xu et al. .................. 356/237.3 |
| 2005/0122508 A1 * | 6/2005 | Uto et al. ................. 356/237.2 |

FOREIGN PATENT DOCUMENTS

| JP | 05-041194 | 2/1993 |
| JP | 2001-133417 | 5/2001 |
| JP | 2003-007243 | 1/2003 |

* cited by examiner

*Primary Examiner*—Robert Kim
*Assistant Examiner*—Michael Maskell
(74) *Attorney, Agent, or Firm*—Antonelli, Terry, Stout & Kraus, LLP.

(57) ABSTRACT

The invention provides an apparatus and a method each capable of highly accurately reviewing at a high speed very small foreign matters and pattern defects occurring during a device production process for forming a circuit pattern on a substrate of semiconductor devices, etc. An objective lens having high NA is installed inside a vacuum chamber for an inspection object having a transparent film formed on the surface thereof and an illumination optical path is formed inside the objective lens so that dark visual field illumination can be made and reflected and scattered light of foreign matters or defects on the surface of the inspection object can be detected with high sensitivity.

15 Claims, 11 Drawing Sheets

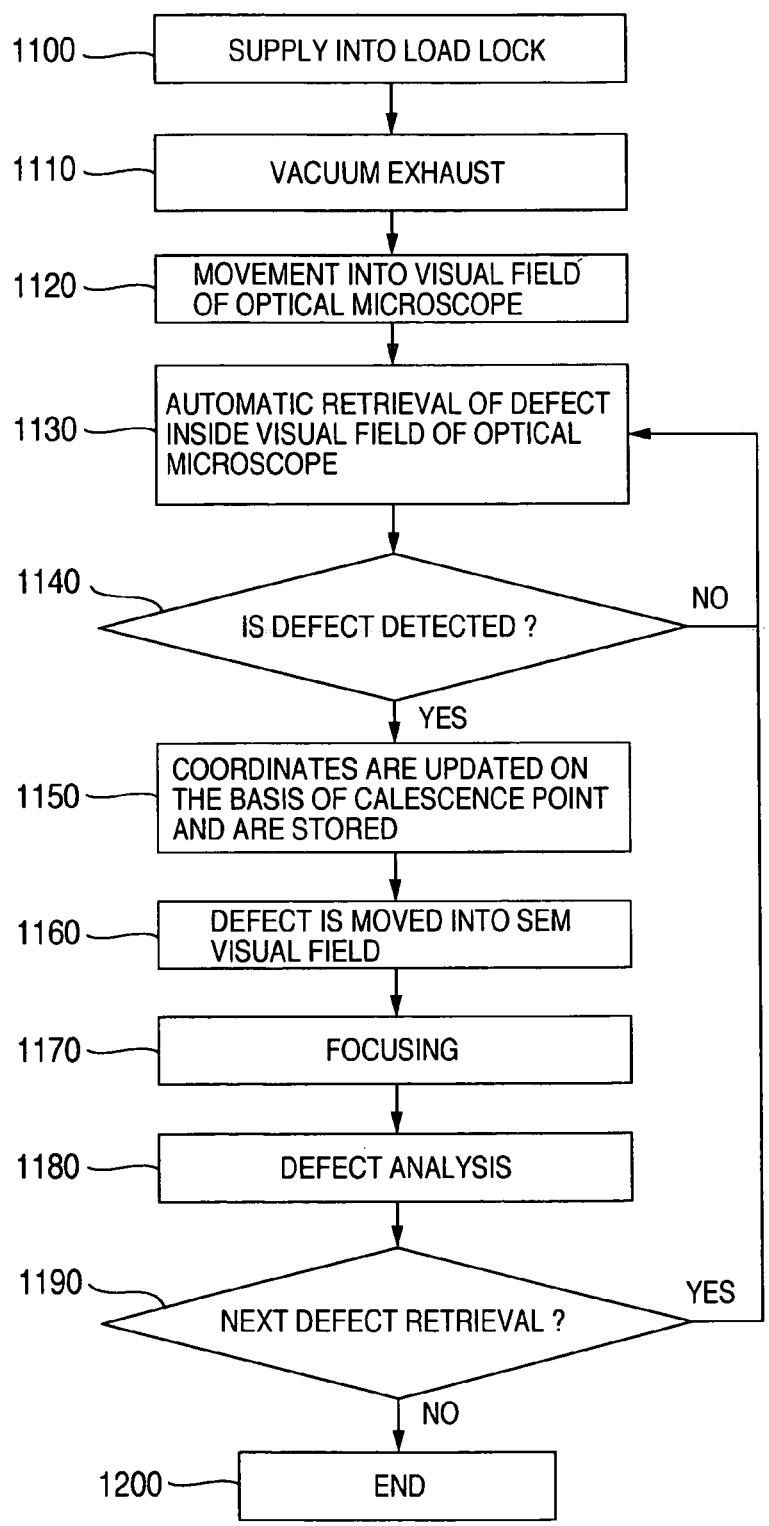

METHOD AND APPARATUS FOR REVIEWING DEFECTS

INCORPORATION BY REFERENCE

The present application claims priority from Japanese application JP2005-261563 filed on Sep. 9, 2005, the content of which is hereby incorporated by reference into this application.

BACKGROUND OF THE INVENTION

This invention relates to a method for reviewing a defect occurring in a semiconductor production process and an apparatus for the method. More particularly, the invention relates to a method for reviewing a defect, and an apparatus for the method, that will be suitable for reviewing in detail a defect by using an electron microscope.

Foreign matters, if any, on a semiconductor substrate (wafer) may result in defects such as inferior insulation and short-circuit of wiring in a semiconductor production process. With miniaturization of semiconductor chips, finer foreign matters may result in insulation defects of capacitors and breakdown of a gate oxide film. These foreign matters are generated for various causes such as those which occur from movable portions of a conveyor apparatus, those occurring from the human body, those formed as reaction products of a process gas inside a processing apparatus, those mixing in chemicals and materials, and they mix in various forms under various states. Examples are scratches on the semiconductor wafer, residues of the materials, particles, and so forth, and all of them affect production through-put.

It is therefore necessary to detect the defects occurring on the semiconductor substrate during the production process, to classify the defects detected and to identify in an early stage the occurrence source of the defects, and to prevent the mass occurrence of defects.

As a method of clarifying the causes of such defects, a method has been employed in the past that involves the steps of applying dark visual field illumination to the surface of the semiconductor substrate by using an optical foreign matter inspection apparatus to detect scattered light from the foreign matters and to stipulate the positions of defects, or detecting a bright visual field optical image of the semiconductor substrate by using an optical appearance inspection apparatus, comparing this optical image with a reference image to stipulate the positions of the defects on the semiconductor substrate, reviewing in detail the defects the position of which are stipulated through an SEM (Scanning Electron Microscope), classifying the defects, comparing them with a database and estimating the occurrence causes of the defects. Such a reviewing method is disclosed in JP-A-2001-133417, JP-A-2003-007243 and JP-A-05-041194.

To improve through-put of inspection when the foreign matters on the surface of the semiconductor substrate are detected by using the optical foreign matter inspection apparatus, the spot size of a laser beam for the dark visual field illumination of the semiconductor substrate surface is increased and the surface of the semiconductor substrate is scanned. Therefore, accuracy of the position coordinates determined from the position of the laser beam spot that scans the semiconductor substrate surface contains a large error component.

When the defect is reviewed in detail by using the SEM on the basis of the position information of the defect containing such a large error component, the defect to be reviewed is not contained in some cases in the image of the SEM that reviews the image in an incomparably higher magnification ratio than the optical foreign matter inspection apparatus. To bring the image of the defect to be reviewed into the visual field of the SEM in such a case, the defect is searched out while being moved inside the visual field of the SEM, but this is time consuming and results in the drop of through-put of the SEM observation.

The optical appearance inspection apparatus executes bright visual field illumination of the semiconductor substrate as the reviewing object and compares the image taken with a reference image to detect the defect. When the surface of the semiconductor substrate is covered with an optically transparent film, however, a defect existing inside or below the optically transparent film is detected, too, besides the defect existing on the surface of this film.

When the defect is reviewed in detail by the SEM on the basis of the position information of the defect detected by the optical appearance inspection apparatus, the defect detected by the optical appearance inspection apparatus and existing inside or below the film cannot be detected by the SEM because the SEM can generally acquire only the information of the sample surface. In such a case, the inspection apparatus using the SEM is likely to conclude that the optical appearance inspection apparatus makes wrong detection.

SUMMARY OF THE INVENTION

When a defect detected by an optical foreign matter inspection apparatus or an optical appearance inspection apparatus is reviewed in detail by using an SEM, the invention provides a defect reviewing method, and an apparatus for the method, capable of reliably carrying the defect detected by the optical foreign matter inspection apparatus or the optical appearance inspection apparatus into an observation visual field of the SEM.

In a defect reviewing apparatus including storage means for storing in advance position information of a defect that is acquired in advance through detection of a substrate having a pattern formed thereon and covered with an optical transparent film by other inspection apparatus, defect reviewing means having an illumination system for illuminating a defect and a detection optical system for detecting a defect, stage means for positioning a defect on a sample surface to be reviewed on the basis of position information of the defect stored in the storage means by putting the substrate into the visual field of the detection optical system, and electron microscope means for reviewing the defect detected by the defect reviewing means, wherein the illumination system includes a first illumination portion for illuminating the substrate at a large incidence angle and a second illumination portion for illuminating the substrate at a small incidence angle, the detection optical system further includes a shading portion for cutting off a diffraction light image from the pattern of the substrate illuminated by the illumination system, the defect to be reviewed is positioned inside the visual field of the detection optical system of the defect reviewing means on the basis of the position information of the defect acquired in advance through detection by using other inspection apparatus and stored in the storage means, the defect positioned inside the visual field is illuminated by the illumination system and the diffraction light image from the pattern by the illumination of the detection optical system is detected by shading, whether the defect exists on the surface of the optically transparent film or inside or below the optically transparent film is distinguished on the basis of the signal so detected, and the defect that is distinguished as existing on the optically transparent film is reviewed through an SEM.

When the defect detected by the optical foreign matter inspection apparatus or the optical appearance inspection apparatus is reviewed in detail by using the SEM, the invention makes it possible to reliably bring the defect detected by the optical foreign matter inspection apparatus or the optical appearance inspection apparatus into the observation visual field of the SEM and to improve through-put of the detailed examination of the defect using the SEM.

These and other objects, features and advantages of the invention will be apparent from the following more particular description of preferred embodiments of the invention, as illustrated in the accompanying drawings.

BRIEF DESCRIPTION OF THE DRAWINGS

FIG. 14 is a flowchart for the SEM observation of the defect detected by the defect reviewing apparatus;

DESCRIPTION OF THE INVENTION

Preferred embodiments of the invention will be hereinafter explained with reference to the accompanying drawings.

Figure 1:
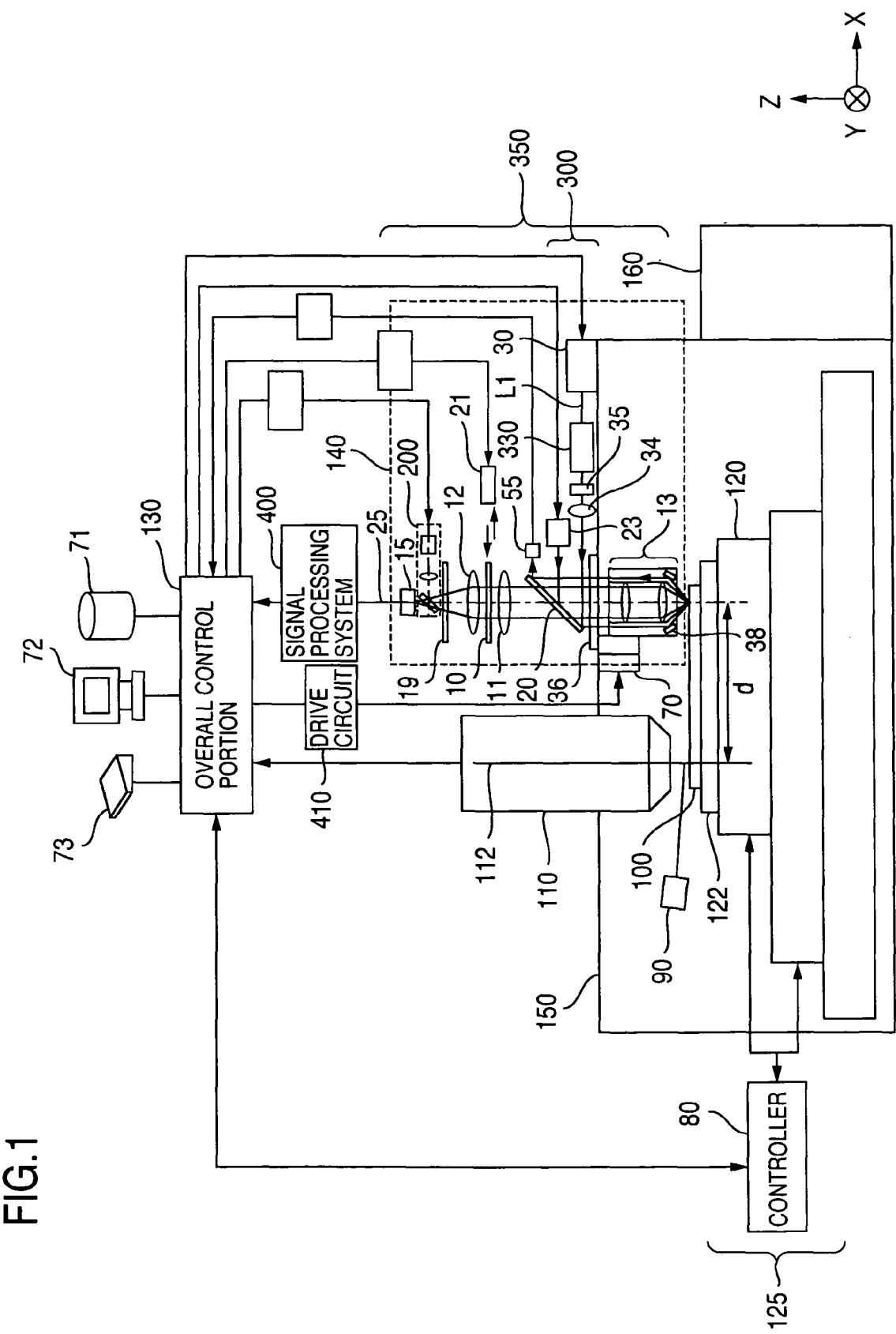
FIG. 1 is a front view showing a schematic construction of a surface defect reviewing apparatus according to an embodiment of the invention.

A defect reviewing apparatus on an article surface according to the invention includes a scanning electron microscope (SEM) 110, a defect detection device 140, a conveyor system 125, a load lock chamber 160 having these members assembled therein, a vacuum chamber 150 having vacuum exhaust means not shown, and an overall control portion 130 as shown in FIG. 1.

The conveyor system 125 includes an XY stage 120 for placing and moving reviewing object substrates 100 fabricated from various production processes such as wafers, and a controller 80.

The defect reviewing apparatus 140 includes a dark visual field illumination system 300 for setting a laser beam L1 outgoing from a laser beam source 30 to a certain size by beam diameter varying means 330 and then irradiating the laser beam from an obliquely upward direction of the reviewing object substrates 100 through a wavelength plate 35, a beam splitter 20 and a mirror 38, and a detection optical system 350 including an objective lens 13, a beam splitter 20, a first lens group 11, a spatial filter 10, a second lens group 12, an optical filter 19 and an optical detector 15 such as CCD that are placed on an XY table 120 for placing the reviewing object substrates 100.

An image signal 25 outputted from the optical detector 15 inside the detection optical system 350 is processed by a signal processing system 400 and a defect is detected and transmitted to the overall control portion 130 for controlling an overall sequence. The overall control portion 130 includes an input/output section 73 (inclusive of a keyboard and a network), a display portion 72 and a storage portion 71.

On the other hand, the scanning electron microscope (SEM) 110 is arranged in such a fashion that an electron beam axis 112 exists coaxially in a Y direction and is spaced apart by a distance d in an X direction with respect to the defect detection apparatus 140 described above. The scanning electron microscope (SEM) 110 is the apparatus that irradiates and scans the electron beam to the reviewing object substrate 100 and reviews the image in a high magnification by detecting secondary electrons emitted from the reviewing object substrate 100. Defect map data as positional information of defects on the reviewing object substrate 100 outputted from another reviewing apparatus is inputted through the input/output portion 73 (inclusive of the keyboard and the network) and the XY stage 120 is moved at a position substantially coincident in the XY direction with the electron beam axis 112 of the scanning electron microscope (SEM) 110 on the basis of the defect map data. The position in the Z direction on the reviewing object substrate 100 is detected by a focus detection system 90 (only the projection side is shown and the reception side is omitted in FIG. 1) and the defect of the reviewing object substrate 100 is reviewed while the focus of the electron beam is controlled by the overall control portion 130 so that the SEM image becomes clear. Incidentally, a secondary electron detector (not shown in the drawings) is constituted by a photo-electric converter or an EDX (Energy Dispersive X-ray spectroscopy) that is so arranged as to face the point of intersection between the electron beam axis 112 and the reviewing object substrate 100.

Next, the dark visual field optical system 300 will be explained with reference to FIGS. 2A, 2B and 3. The laser beam L1 outgoing from the laser beam source 30 passes through a shutter 31 that is opened and closed by a driving signal from the overall control portion 130 (see FIGS. 2A and 2B), then through the beam diameter varying means 330, the wavelength plate 35 and the lens 34, is reflected downward by the beam splitter 20, transmits through a transparent window portion 36, is incident into the objective lens 13 disposed inside the vacuum chamber 150, is reflected by the mirror 38a and is irradiated from an obliquely upward direction to the surface of the reviewing object substrate 100. At this time, scattered light S1 (see FIG. 3) from the defect 5 of the surface of the reviewing object substrate 100 reaches the detection optical system 350 having an optical axis 312 and normal reflected light L2 reaches a mirror 38b disposed at a symmetric position with respect to the optical axis of the detection optical system 350 of the mirror 38a and is reflected upward.

Figure 2A:
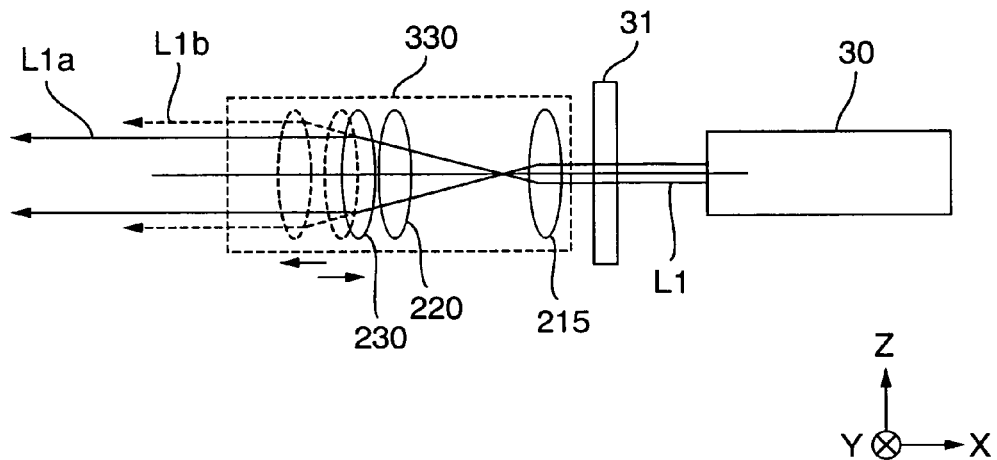
FIG. 2A is a front view showing a schematic construction of an illumination optical system.
Figure 2B:
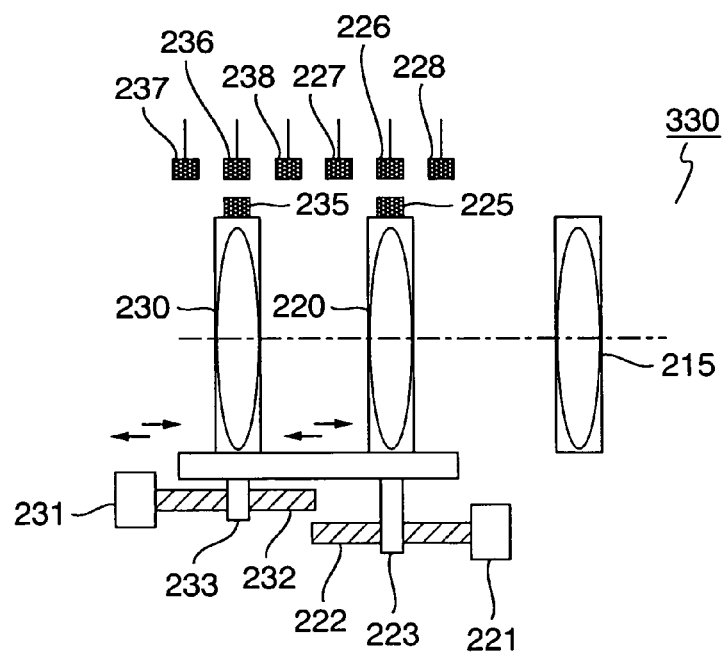
FIG. 2B is a front view showing a schematic construction of beam diameter varying means.
Figure 3:
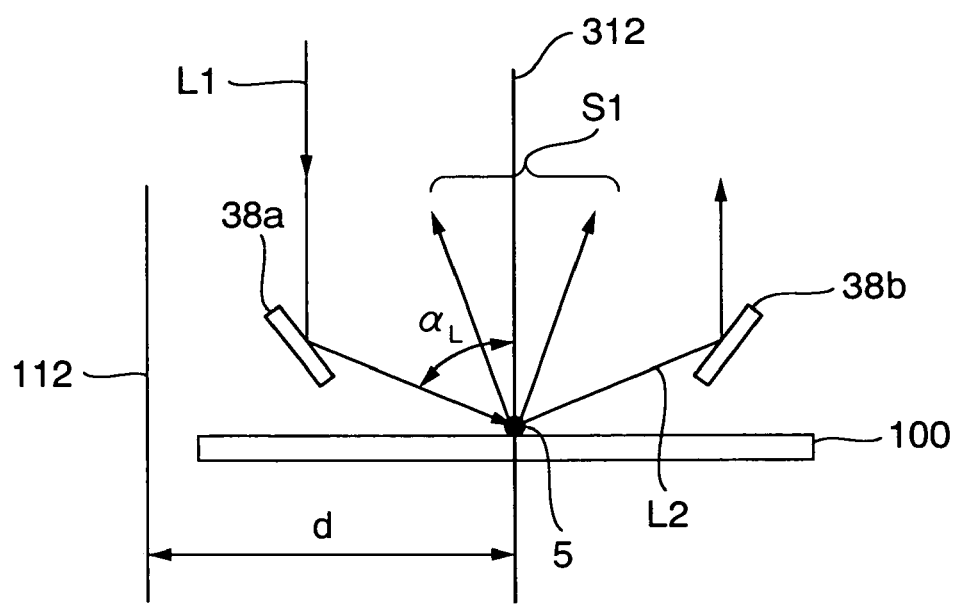
FIG. 3 is a front view showing a schematic construction of the illumination optical system shown in FIG. 1.

The beam diameter varying means 330 includes three groups of lenses 215, 220 and 230 having mutually different focal lengths as shown in FIGS. 2A and 2B, for example. The lens 220 is moved in the direction of optical axis (X direction) by a motor 221 (a pulse motor, for example) and a feed screw 222 through a lens holding portion 223. The lens 230 is moved in the direction of optical axis (X direction) by a motor 231 and a feed screw 232 through a lens holding portion 233. The diameter of the laser beam incident to the lens 34 can be changed by changing the gap between the lens 220 and the lens 230 in the X direction and the irradiation range of the laser beam irradiated to the surface of the reviewing object substrate 100 becomes variable.

In other words, after the position of an origin sensor 226 is detected by a movable portion 225 of a positioning sensor disposed at the distal end of the lens holding portion 223, the rotation pulse of the motor 221 is controlled by the driving signal from the overall control portion 130 through a controller (not shown in the drawings). Sensors 227 and 228 are limit sensors that are so installed as to interpose the origin sensor 226 between them. An optical or magnetic sensor can be used for the positioning sensor. These operations are carried out by the instruction from the overall construction portion 130 and setting of the illumination range is made in synchronism with a detection magnification of the detection optical system 350. Incidentally, the illumination range is determined by the beam diameter by the beam diameter varying means 330 and the focal length of the lens 34, and the data of the relation between the beam diameter and the focal length (beam diameter variable means 330 and lens 34) is stored in advance in the overall control portion 130.

Figure 4:
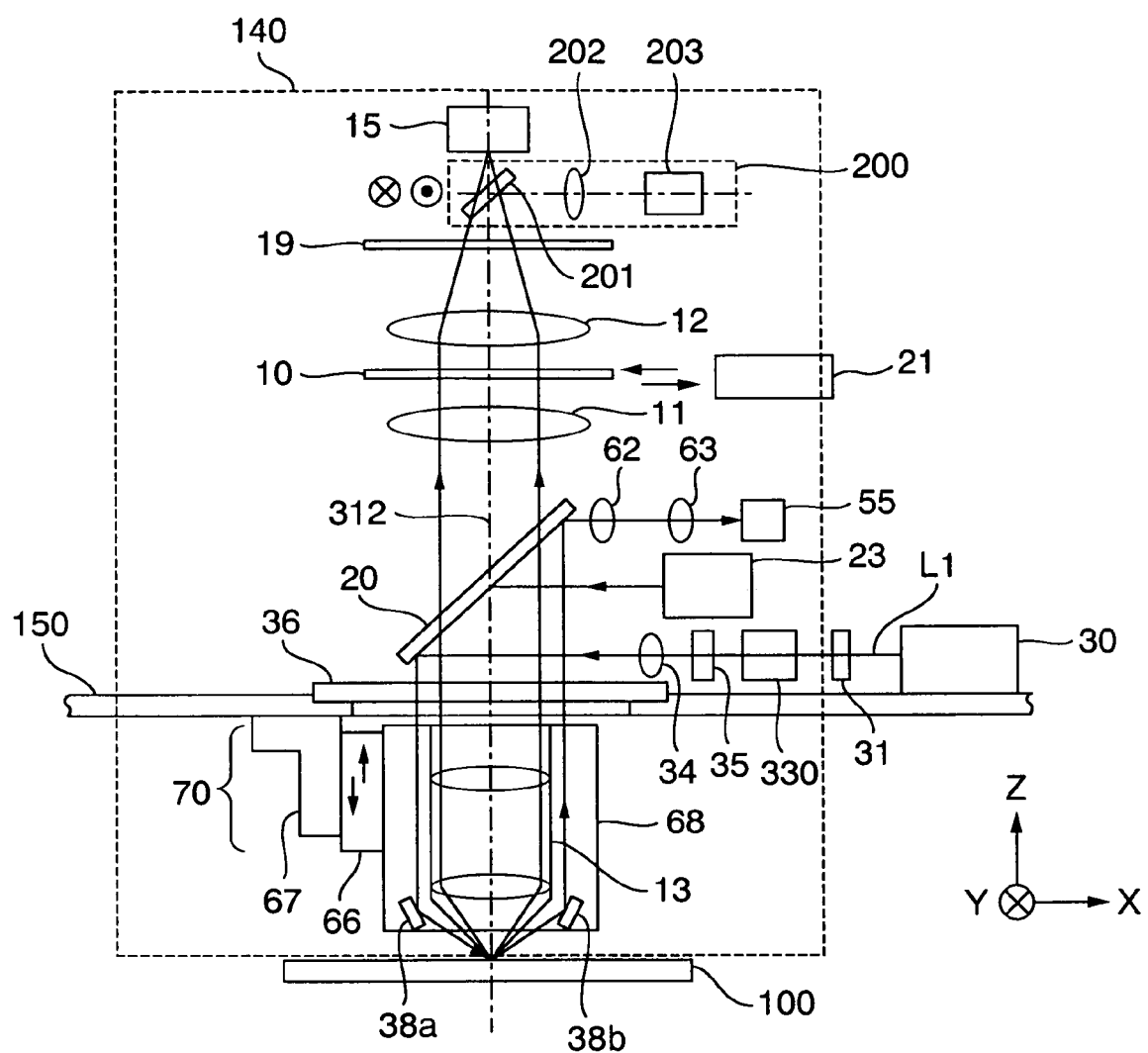
FIG. 4 is a front view showing a schematic construction of the detection optical system shown in FIG. 1.

Next, the detection optical system 350 will be explained. The detection optical system 350 includes the objective lens 13, the beam splitter 20, the first lens group 11, the spatial filter 10, the second lens group 12, the optical filter 19 and the optical detector 15 as shown in FIG. 4 and detects light (scattered light) reflected and scattered by the defect 5 from above the reviewing object substrate 100. To detect a finer defect, a detection NA (numerical aperture) of the objective lens is preferably greater. When the NA is increased, however, the operation distance becomes smaller and laser illumination from outside the objective lens becomes more difficult.

As means for solving these problems, the invention arranges the objective lens 13 inside the vacuum chamber 150, brings it close to the reviewing object substrate 100 to achieve the high NA detection, irradiates the laser to the reviewing object substrate 100 from the oblique direction through the inside of the lens barrel 68 of the objective lens 13 and condenses the beams reflected and scattered (scattered light) by the reviewing object substrate 100 by the objective lens 13. The optical detector 55 detects the beams so condensed to thereby conduct dark visual field detection while the position detector 55 detects normal reflected light from the reviewing object substrate 100 to determine the fluctuation of the surface of the reviewing object substrate 100 in the direction of height (Z direction). The objective lens 13 is moved finely in the Z direction by an actuator 70 to correct the fluctuation of the focal point.

In other words, the objective lens 13 is arranged inside the vacuum chamber 150 through the actuator 70 capable of fine movement in the Z direction and the actuator 70 is finely moved in the Z direction by the signal from the overall control portion 130 through the drive circuit 410 to adjust the focus. The mirror 38 is fixed to the lens barrel that supports the objective lens 13, and is moved in the Z direction together with the objective lens 13 when driven by the actuator 70. The laser illumination beam L1 is reflected by the mirror 38a and is irradiated to the surface of the reviewing object substrate 100. The mirror 38b that is disposed at a symmetric position with the mirror 38a on exactly the opposite side of the laser illumination beam reflects the laser beam reflected on the surface of the reviewing object substrate 100 in the Z direction.

After reflected by the beam splitter 20, the laser beam reaches the position detector 55 through the lens 62 and the lens 63. The surface of the reviewing object substrate 100 and the light reception surface of the position detector 55 have an image formation relation. The position detector 55 is a photoelectric element the light reception surface of which is divided into two or four parts and each divided element outputs an electric signal in accordance with the intensity of the beam received. The position signal outputted from the position detector 55 is processed by a processing circuit 190 and is sent to the overall control portion 130. The processing circuit 190 calculates a difference signal of the output signals of the divided elements of the position detector 55. The overall control portion 130 calculates the X direction position of the position to which the laser beam is irradiated on the reviewing object substrate 100 (X coordinates position of the laser-irradiated position on the reviewing object substrate 100) from the output signal of the processing circuit 190, compares the value with a set value that is in advance stored as a focal position of the objective lens 13, and drives and controls the actuator 70 through the drive circuit 410 so that the laser irradiation position and the optical axis 312 of the objective lens 13 are coincident with each other.

Figure 12:
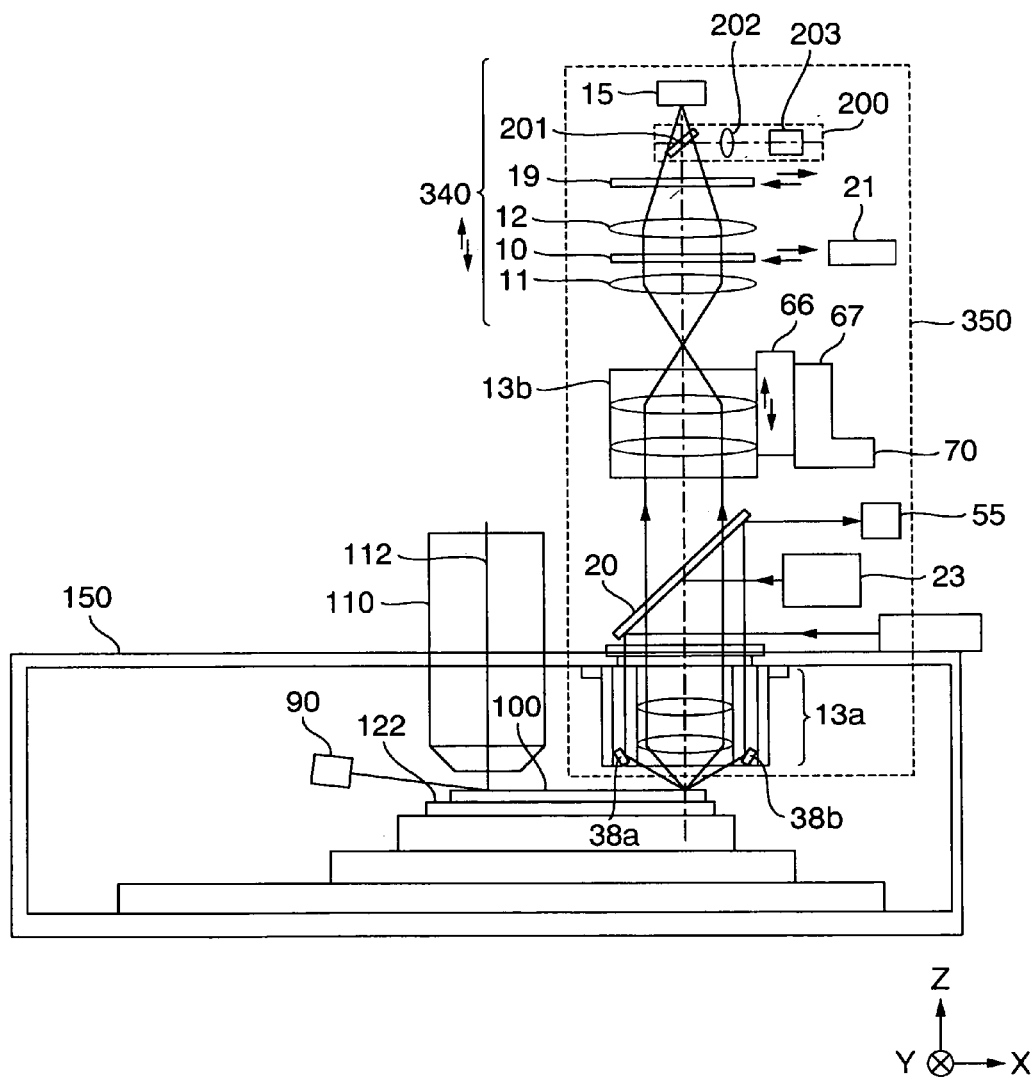
FIG. 12 is a structural view showing a defect reviewing apparatus according to still another embodiment.
Figure 13:
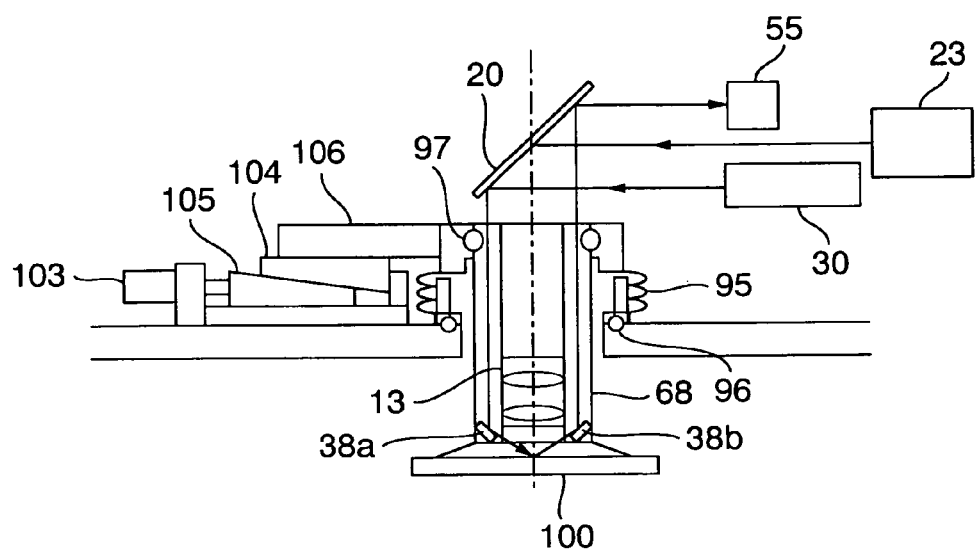
FIG. 13 is a structural view showing a detection optical system according to still another embodiment.

FIG. 12 shows another construction of the detection optical system 350 including the objective lens 13 that is arranged inside the vacuum chamber 150 of the SEM. As shown in this drawing, the objective lens 13a is fixed inside the vacuum chamber 150 and a similar objective lens 13b is disposed on the atmospheric side. The change of the focus with the reviewing object substrate 100 can be corrected by driving the objective lens 13b disposed on the atmospheric side 13b through the actuator 70. In this case, however, the moving distance of the focus between the reviewing object substrate 100 and the objective lens 13a and the output of the position detector 55 are measured in advance and the objective lens 13b is moved in the Z direction in accordance with the output signal of the position detector 55. A second image formation system 340 of the detection optical system 350 must be moved simultaneously in the Z direction, too. Means for driving the objective lens 13 in the Z direction outside vacuum has the following construction. The objective lens 13 is supported by vacuum bellows 95 as shown in FIG. 13 and O-rings 96 and 97 are disposed at the bond portion for vacuum cutoff. Driving means disposed in the atmosphere moves the objective lens 13. An inclination block 104 is driven by a motor 103 and a feed screw 105 and a support plate 106 at which the objective lens 13 is supported is operated in the Z direction.

On the other hand, scattered light of the defect passes through the objective lens 13, then passes through an incidence window 36 and a beam splitter 20, reaches the optical detector 15 through the first lens group 11, the spatial filter 10 and the second lens group 12 and is detected as an image. The incidence window 36 is a transparent window interposed between the objective lens 13 and the beam splitter 20 and keeps the degree of vacuum inside the vacuum chamber 150 through a vacuum seal member not shown in the drawing. The optical detector 15 is a CCD (charge coupled device), an EBCCD or a TDI sensor time delay integration sensor) in which light reception chips (pixels) are arranged in a direction of single- or two-dimensions, for example, and has a function of varying the light reception accumulation time. The electric signal 25 outputted from the optical detector 15 is processed by the signal processing portion 400, and the processing result is sent to the overall control portion 130.

Incidentally, the beam splitter 20 has the construction that can be switched depending on the dark visual field illumination and the bright visual field illumination. In other words, a beam splitter 20 having a round open portion corresponding to the aperture number of the objective lens with the optical axis 312 being the center and bored at the center of the optical axis is used for the dark visual field illumination. Consequently, an illumination beam outgoing from the laser beam source 30 is reflected and the scattered beam from the defect 5 on the surface of the reviewing object substrate 100 is 100% transmitted. On the other hand, a beam splitter 20 used for the bright visual field illumination is a translucent mirror as a whole so that a half of the beam incident to the beam splitter 20 is reflected and the remaining half is transmitted. These illuminations can be switched by a mechanism not shown in the drawing.

Figure 5A:
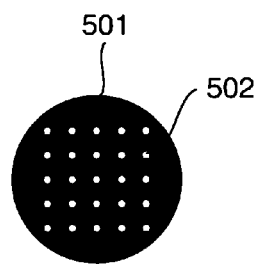
FIG. 5A shows a reflected diffraction optical image from a repetition pattern at a Fourier transform position observed in a pupils reviewing optical system.
Figure 5B:
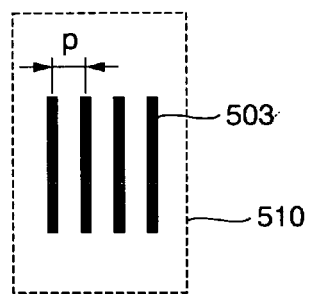
FIG. 5B is a plan view of a shading plate.
Figure 5C:
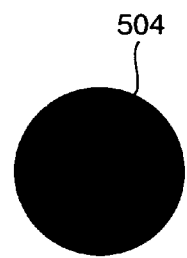
FIG. 5C shows an image reviewed by the pupil reviewing optical system when the shading plate is arranged at the Fourier transform position.

The spatial filter 10 is arranged at the Fourier transform position of the objective lens 13 (corresponding to the outgoing pupil) and cuts off the reflected beam from the reviewing object substrate 100 that may become the noise for detecting the defect and foreign matters (Fourier image owing to reflected diffraction beam from regular repetition pattern, etc, for example). A pupil observation optical system 200 including a mirror 201 capable of moving back in the Y direction during the observation, a projection lens 202 and a TV camera 203 is disposed in an optical path of the detection optical system 350, for example. A reflected diffraction beam image 501 from the repetition pattern at the Fourier transform point shown in FIG. 5A is taken by the TV camera 203 and a calescence point 502 of the diffraction image is cut off by a shading plate 510 having a rectangular shading pattern 503 as shown in FIG. 5B. The shading pattern 503 can change the gap P by a mechanism not shown in the drawing and makes adjustment so that the image obtained by the TV camera 203 becomes an image 504 not having a calescence point as shown in FIG. 5C.

This adjustment is executed by the steps of imaging the reflected diffraction beam image 501 from the repetition pattern at the Fourier transform position by the TV camera 203, processing the signal so obtained by imaging by the signal processing portion 400 to determine the position of the calescence point 502 at the Fourier transform position, and outputting a control signal for control the gap P of the shading pattern 503 from the overall control portion 130 by using the positional information of the calescence point 502 and changing the gap P by a mechanism not shown in the drawing. Under the state where the calescence point 502 by the reflected diffraction beam image 501 from the repetition pattern is cut off by controlling the gap P of the light shading pattern, an image of a certain region of the regular repetition pattern on the reviewing object substrate 100 is taken and portions at which the luminance signals detected exceed a predetermined level are detected as the defects.

Incidentally, the spatial filter 10 can be moved into and back from the optical path by moving means 21. When the image of a region of the reviewing object substrate 100 not having the regular repetition pattern is taken, the spatial filter 10 is moved back from the optical path by the moving means 21. At this time, applicants for the defect can be detected by extracting non-coincident portions by comparing the reviewing region on the reviewing object substrate 100 with the image of the region in which the same pattern exists.

When the defect on the reviewing object substrate 100 is reviewed by an electron microscope, the reviewing object substrate 100 is taken out by a robot arm from a substrate cassette not shown in the drawing, is conveyed onto a table 122 of an XY stage 120 by a conveyor system 125 and is fixed after positioning. Next, the defect of the reviewing object is positioned to the position of the optical axis of the detection optical system 350 on the basis of the defect map data inputted in advance from the input/output portion 73 to the overall control portion 130 and outputted by other reviewing apparatus. The image of the defect is acquired by the optical detector 15 and is inputted to the signal processing system 400. The signal processing system 400 executes the defect detection processing from the image inputted and outputs the result to the overall control portion 130.

The overall control portion 130 outputs the driving signal to the XY stage 120 through the drive circuit. The XY stage 120 moves in the X direction by the distance d between the electron beam axis 112 of the electron microscope and the optical axis 312 of the detection optical system 350 and the defect detected by the defect detector 140 is moved onto the electron beam axis 112 of the electron microscope. Confirmation and analysis of the defect is then made. The display portion 72 can switch the reviewing image of the electron microscope and the image acquired by the optical detector 15, or can display and review them on the same screen. When the defect is not detected by the signal processing system 400, the detection visual field on the reviewing object substrate 100 of the detection optical system is enlarged or diminished to find out the defect. With this enlargement or diminishment, the illumination range of the laser beam L1 is changed by moving the lenses 220 and 230.

Figure 6A:
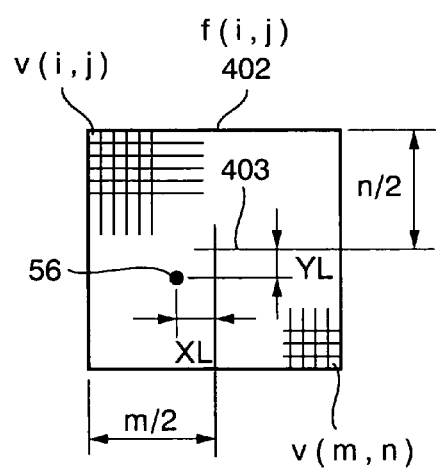
FIG. 6A is a plan view of a light reception surface of a light detector.
Figure 6B:
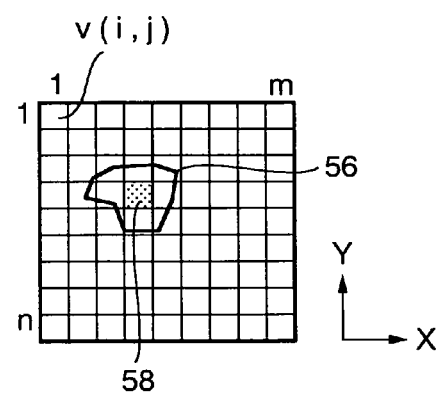
FIG. 6B is a plan view of the light detector showing the state where an image of a defect is projected on the light reception surface.
Figure 7:
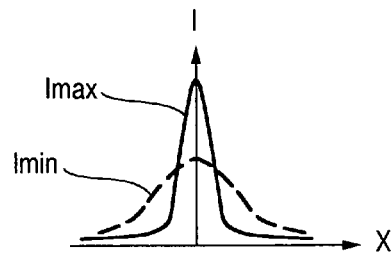
FIG. 7 is a graph of an image signal waveform representing a sectional profile of the defect image shown in FIG. 6.

Next, the operation of detecting the defect from the acquisition image of the optical detector 15 will be explained. FIGS. 6A and 6B are schematic views of a light reception surface of the optical detector 15, wherein the light reception surface is constituted by m×n pixels. The defect on the surface of the reviewing object substrate 100 generates scattered light by the laser beam L1 from the laser beam source 30 or by the illumination from the bright visual field light source 23, and forms the image as a defect image 56 on the light reception surface 402 of the optical detector 15. The defect image is taken from the optical detector 15 into the signal processing portion 400 in the following way. Basically, the objective lens 13a and the reviewing object substrate 100 have the co-focal relation owing to the output signal of the position detector 55. Focusing of the objective lens 13 is adjusted by moving step-wise the actuator 70 by a predetermined amount in the Z direction and the Z position at which the luminance value I of the defect image 56 in the X (Y) direction shown in FIG. 6 attains the maximum value Imax is set as the co-focal point. The difference XL, YL between the center position 403 of the light reception surface 402 and the defect image 56 is calculated for the image at this time and is used as an offset value when the defect is moved to the position of the electron beam axis of the electron optical system.

Figure 8:
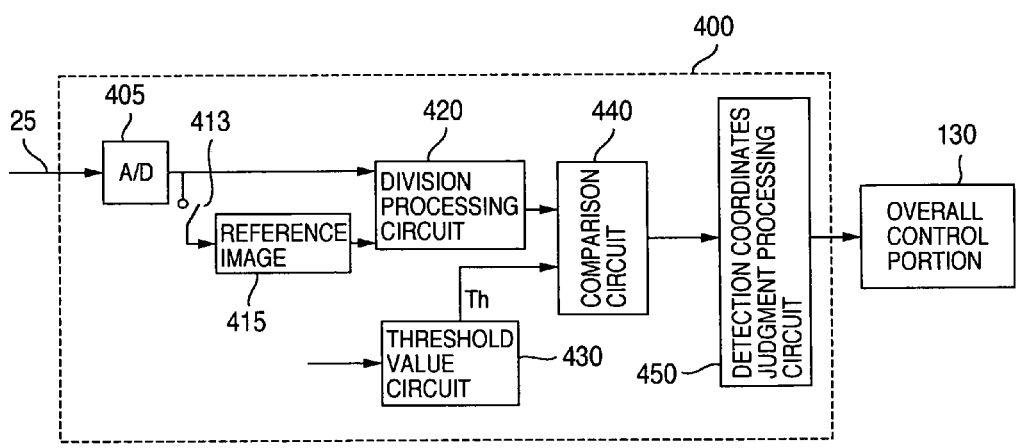
FIG. 8 is a block diagram for explaining the content of a signal processing portion shown in FIG. 1.

When the defect extends to a plurality of pixels as shown in FIG. 6B, the centroid pixel 58 is stored as typical coordinates of the defect. FIG. 8 shows a construction of the signal processing portion 400. The image signal 25 outputted from the detector 15 is subjected to the analog-digital conversion by an A/D converter 405 and is inputted to a division processing circuit 420. The division processing circuit 420 positions of a reference image 415 not containing defect information and the image outputted from the detector 15, executes division for each pixel and outputs the result to a comparison circuit 440.

The comparison circuit 440 compares a threshold value Th outputted from a threshold circuit 430 with the output of the division processing circuit 420 for each pixel. In other words, the threshold value Th is set for a brightness signal v(i, j) of each pixel of a two-dimensional image f(i, j) and whether or not each pixel exceeds the threshold value is judged. The result is outputted by setting the pixels exceeding the threshold value to "1" and those not exceeding, to "0", to a detection coordinates judgment processing circuit 450. The detection coordinates judgment processing circuit 450 selects the "1" pixel among the inputted image signals as the defect applicant and the pixel at the centroid position as the defect coordinates, stores them in the overall control portion 130, compares them with defect map coordinates of other reviewing apparatus, updates the coordinates position when the coordinates of both of them are greater than the visual field of the detection optical system 350 on the wafer 100 of the optical detector 15 and looks up the coordinates of the defect map at other times. A shading image of illumination light acquired prior to reviewing or image data of a chip or memory cell repeatedly formed on the reviewing object substrate 100 is used as a reference image 415. The pattern image that should be originally similar to the pattern of the reviewing object of the chip or memory cell portion adjacent to, or in the proximity of, the defect coordinates during the movement of the XY stage 120 under the state where the spatial filter 10 is arranged in the optical path of the detection optical system 350 can be selected by opening and closing a switch disposed inside the circuit.

Incidentally, a multi-layered wafer is fabricated by repeating the formation of a transparent film (oxide film, for example) 804 on the surface of the reviewing object substrate 100 during a multi-layer configuration process and the formation of the pattern on the former. Needs have increased for detecting only a foreign matter 803 and a pattern defect on the surface of the oxide film on the wafer on which the oxide film is formed. According to an optical pattern inspection apparatus or foreign matter inspection apparatus, the illumination beam reaches the inside of the transparent film and is irradiated to the defect inside the film, and not only the defect and foreign matter on the surface of the transparent film but also the defect 802 inside the transparent film 802 are detected. Therefore, it is believed that the inspection map of the inspection apparatus described above contains both of them in mixture.

However, it has been believed difficult to review the defect 802 inside the transparent film by using the SEM. Therefore, even when the defect coordinates are positioned immediately below the electron beam axis 112 of the SEM, the defect cannot be confirmed and the result is often regarded as erroneous detection by the pattern inspection apparatus.

Therefore, the present invention employs the following arrangement as will be explained with reference to FIGS. 9A and 9B. Illumination is made by changing the illumination angle by mirrors 38 and 39 arranged in the dark visual field illumination system 300 to adjust transmission and reflection of illumination light to the transparent film and to irradiate a greater quantity of illumination beam to either the surface defect or the in-film defect. The detection optical system 350 judges whether the defect detected by the optical appearance inspection apparatus exists on or inside the film and feeds back the result to the SEM. In other words, the mirror 39 irradiates the defect inside the transparent film by illumination having a small incidence angle (approximate to vertical) while the mirror 38 irradiates a greater quantity of illumination beam to the surface of the transparent film with a greater incidence angle (approximate to horizontal).

In other words, a wavelength plate 35 ($\lambda/2$ plate or $\lambda/4$ plate, for example) arranged in the optical path is rotated by rotation means, not shown, round the optical axis as the center to rotate the direction of linear polarization of the laser beam L1. Total reflection is achieved by the mirror 38 when the laser beam L1 is polarization vertical to the sheet of drawing of FIG. 9 and by the mirror 39 when the laser beam L1 is parallel to the sheet of drawing. Incidentally, the incidence angle of the illumination beam reflected by the mirrors 38 and 39 to the reviewing object substrate 100 (irradiation angle) is set to the optimum value from the result obtained by changing the inclination of the mirrors 38 and 39 to change the irradiation angle.

Figure 9A:
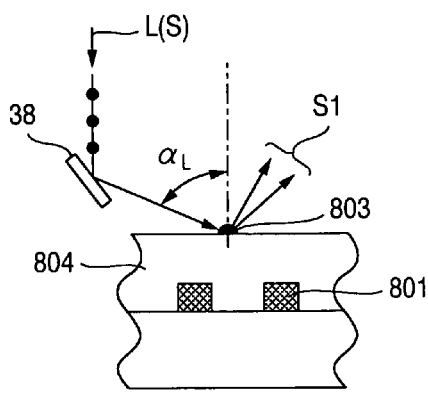
FIG. 9A is a sectional view of a sample showing incidence and reflection of a laser beam to and from a sample surface when the direction of linear polarization of the laser beam is perpendicular to the sheet of drawing.

When the rotation angle of the wavelength plate 35 is adjusted so that the direction of linear polarization of the laser beam L1 is vertical to the sheet of drawing of FIG. 9 in the construction described above, the laser beam L1 is totally reflected by the mirror 38 and is incident into the surface of the sample at an incidence angle $\alpha_L$ as shown in FIG. 9A. The laser beam L1 incident into the transparent film 804 at this incidence angle $\alpha_L$ is mostly reflected by the surface of the transparent film 804 and scattered light S1 is created from the defect 803 on the surface. This scattered light S1 passes through the detection optical system 350 shown in FIG. 1, reaches the optical detector 15 and is detected.

Figure 9B:
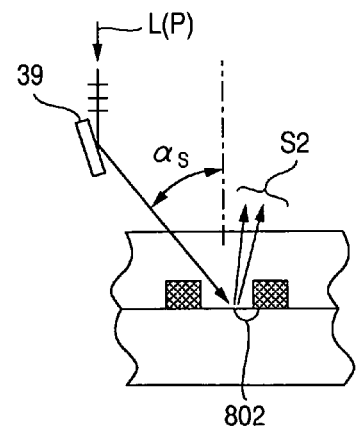
FIG. 9B is a sectional view of the sample showing incidence and reflection of a laser beam to and from a sample surface when the direction of linear polarization of the laser beam is parallel to the sheet of drawing.

On the other hand, when the rotation angle of the wavelength plate 35 is adjusted so as to set the direction of linear polarization of the laser beam L1 parallel to the sheet of drawing in FIG. 9B, the laser beam L1 is reflected by the mirror 39 and is incident to the surface of the sample at an incidence angle $\alpha_S$ as shown in FIG. 9B. The laser beam L1 incident to the transparent film 804 at this incidence angle $\alpha_S$ is irradiated to the defect 803 on the surface to create scattered light S1 from the defect 803 and at the same time, is irradiated to the defect 802 in or below the film to create scattered light S2 from the defect 802. Scattered light S2 from the defect 802 inside the film passes through the optical system 350 shown in FIG. 1 together with scattered light S1 from the defect 803 that exists on the surface, reaches the optical detector 15, and is detected by the optical detector 15.

Illumination by light reflected by the mirror 39 creates scattered light from the defect 803 on the surface of the transparent film 804 and from the defect 802 inside the film. Illumination by light scattered by the mirror 38 does not create scattered light from the defect 802 inside the transparent film 804. Therefore, it becomes possible to distinguish the defect 803 on the surface of the transparent film 804 from the defect 802 existing inside the film by processing the defect signal detected by the optical detector 15 in synchronism with switching of the illumination angle by the mirrors 38 and 39 by using the information of the rotation angle of the wavelength plate 35. In other words, the defect 803 is found existing on the surface of the transparent film 804 both when illumination is made by the mirror 38 and when it is made by the mirror 39. The defect 802 is found existing inside the transparent film 804 when illumination is made by the mirror 38 but the defect is detected when illumination is made by the mirror 39.

Figure 10:
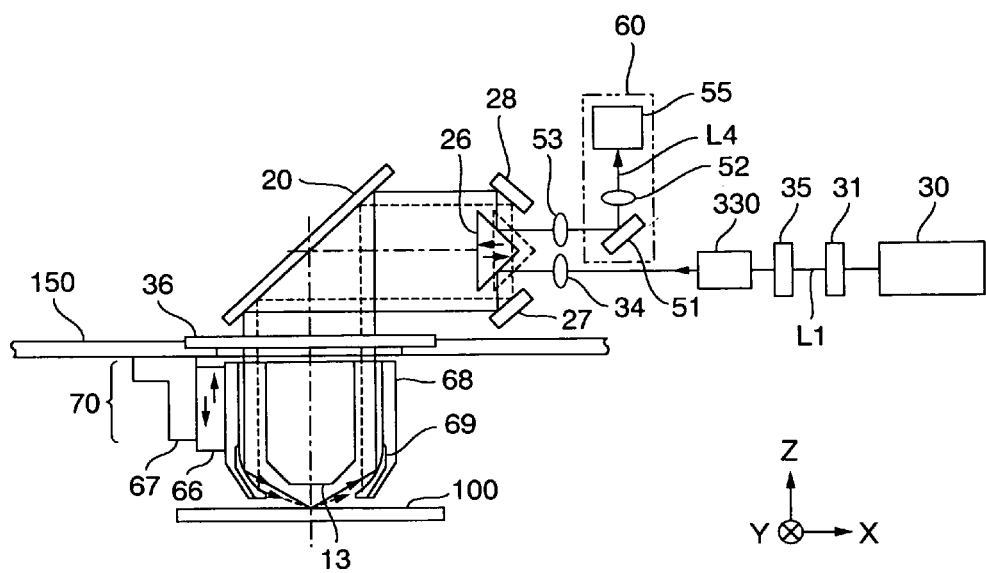
FIG. 10 is a front view showing a schematic construction of an illumination optical system according to another embodiment.

The dark visual field illumination system 10 employs the construction shown in FIG. 10 as an embodiment of the invention on the basis of the concept described above. In other words, to accomplish varying illumination angles, a parabolic mirror 69 having a flat surface in the Y direction and multi-stage parabolic surfaces in the X-Z direction is arranged at a position on the optical axis of the objective lens 13 inside the barrel 68 that supports the objective lens and is symmetric in the Y direction. As a rectangular mirror 26 disposed in the optical path of the dark visual field illumination system 300 is moved by moving means not shown in the drawing, the reflection position of the laser beam L1 outgoing from the laser beam source 30 at the beam splitter 20 is changed in the X direction and reaches, and is reflected by, the parabolic mirror 69, so that the illumination angle to the defect 803 on the surface of the transparent film 804 can be changed. To detect the defect on the surface of the transparent film 804, too, normal reflected light L4 of laser illumination light from the surface of the transparent film 804 is subjected to the image formation by lenses 52 and 53 on the detector 55 and is detected by the detector 55. Consequently, the change of the laser illumination position on the reviewing object substrate 100 can be detected from the position of the detected image and focusing of the objective lens 13 can be made by using the information of this position change.

Figure 11A:
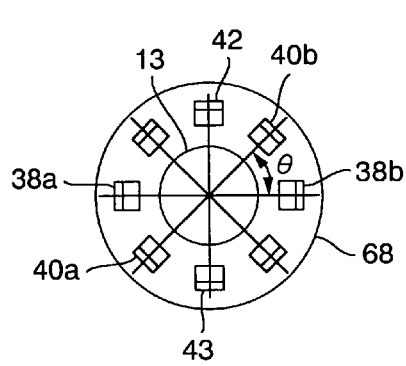
FIG. 11A is a plan view of an objective lens showing the positional relationship among mirrors 38a, 38b, 40a, 40b, 42 and 43, the objective lens and a lens barrel.
Figure 11B:
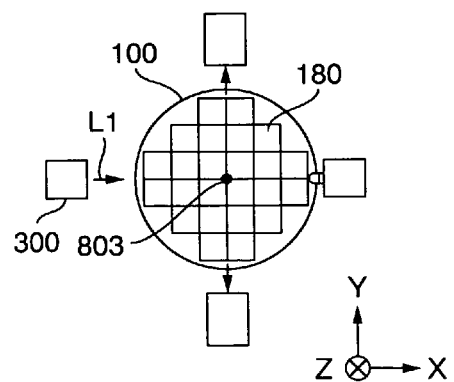
FIG. 11B is a plan view of a reviewing object substrate showing the relation among a position detector 60, an illumination/detection system and the reviewing object substrate.

Here, the mirror 26 disposed in the illumination optical path has a rectangular shape to reflect illumination light reflected by the mirror 38a and irradiated onto the reviewing object substrate 100 by the mirror 38b and to guide it to the position detector 55. As shown in FIG. 11A, mirrors 40a and 40b may be arranged in a direction deviated by an angle θ from the illumination. To detect scattered light from the defect by disposing mirrors 42 and 43 in a θ=90° direction, for example, a rectangular pyramid mirror is disposed in place of the rectangular mirror 26 to cause reflection in four directions. Second detection systems 290 and 291 are arranged at positions rotated by 90 degrees in the Y-Z direction from the illumination and position detection optical path to detect the image by a two-dimensional CCD such as a TV camera. In such a construction, the defect is detected from an oblique direction and this construction can be applied to the defect detection on the outer peripheral end surface of the reviewing object substrate 100 besides the defect detection inside the chip 180 fabricated on the reviewing object substrate 100 as shown in FIG. 11B. In this case, illumination may be made by using the bright visual field light source 23 by switching the beam splitter 20 by means, not shown, as the illumination.

Figure 15A:
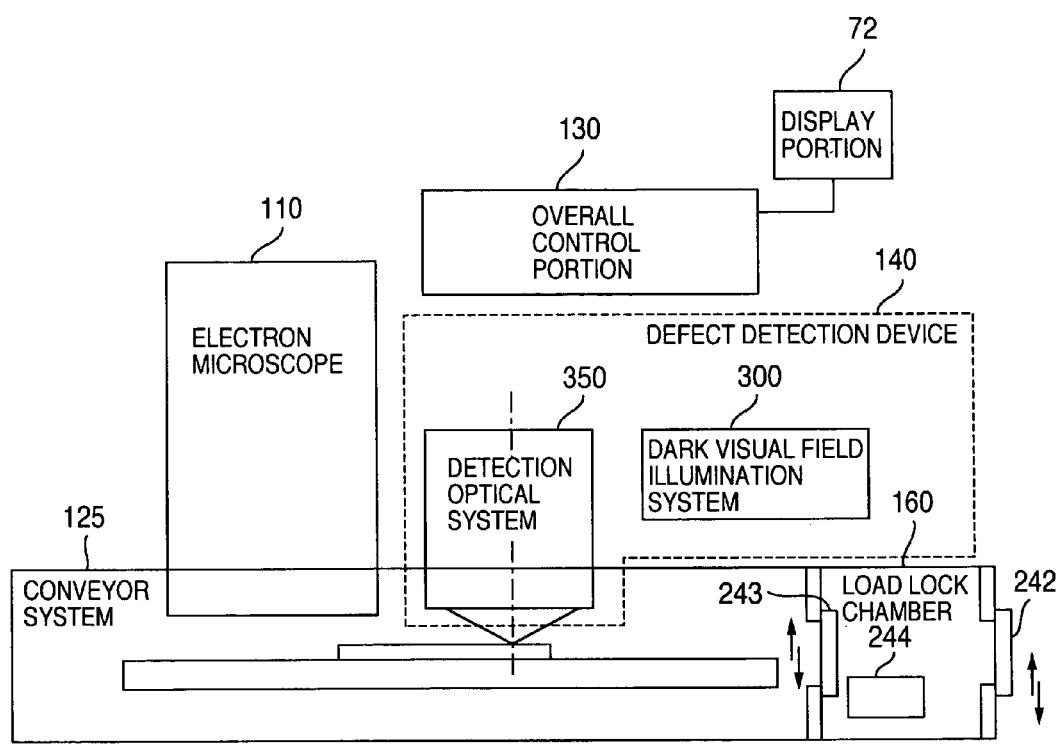
FIG. 15A is a block diagram showing an overall construction of this invention.

Next, the sequence for detecting the defect by using the defect reviewing apparatus of the invention having the construction described above will be explained with reference to FIGS. 14 and 15.

The reviewing object substrate 100 passed through a predetermined process in a device production line is inspected by using an inspection apparatus (optical appearance inspection apparatus for detecting pattern defect or foreign matter inspection apparatus for detecting foreign matters), not shown, and defects on the reviewing object substrate 100 are detected. The position coordinates information of each of the detected defects is transferred to and stored in the overall control portion 130 through communication means not shown in the drawing.

After this defect inspection, the reviewing object substrate 100 is accommodated in and transported by a cassette not shown in the drawing and is supplied to a load lock chamber 160 (S1100) as a gate valve 242 is opened and closed. Vacuum exhaust is executed inside the load lock chamber 160 (S1110). After this vacuum exhaust, a gate valve 243 is opened and closed and the reviewing object substrate 100 is positioned and put onto the XY stage 120 inside the vacuum chamber of the SEM by a conveyor robot 244. Next, the defect coordinates position on the reviewing object substrate 100 is moved to the visual field of an optical microscope on the basis of the defect position coordinates information detected by the inspection apparatus not shown and stored in the overall control portion 130 (S1120). The laser beam is irradiated from the laser beam source 30 to the reviewing object substrate 100 and the calescence point that may become the defect inside the visual field of the optical microscope is automatically retrieved (S1130). When no defect is detected inside the visual field, the retrieval area is increased with the defect coordinates as the reference and the retrieval is again made. When the defect is detected, on the other hand, the coordinates are determined on the basis of the calescence point of the defect detection image of the optical detector 15. The defect coordinates of the inspection apparatus are updated and stored when a difference exceeding the detection visual field from the coordinates of the inspection apparatus occurs (S1150).

The defect detected by the optical microscope is moved by the XY stage 120 to the observation visual field of the SEM. After focusing by the electron beam adjustment of the SEM, the image of the defect is acquired by the SEM (SEM image) and the overall control portion 130 analyzes the SEM image acquired (S1180). In this analysis of the SEM image, feature quantities of the defect image (size of defect, ratio of sizes in X and Y directions, area, centroid position, shape, luminance distribution, etc) are extracted from the SEM image, and the feature quantities thus extracted are compared with classification data stored in advance in the database to classify the defect observed.

Retrieval of the defect by the laser beam is basically carried out by dark visual field illumination but can also be carried out in accordance with the detection system of the inspection apparatus not shown in the drawing. When the inspection apparatus, not shown, that detects the defect position coordinates information stored in the overall control portion 130 is a defect inspection apparatus using the bright visual field illumination, for example, the detection method involves the steps of illuminating the reviewing object substrate 100 by the bright visual field light source 23, taking the image of the surface of the reviewing object substrate 100 by the detection optical system 350, detecting the defect by the retrieving method described above, finely adjusting the XY stage so that the detected defect can be positioned at the center of the visual field and correcting the position information of the defect stored in the overall control portion 130 on the basis of the XY stage finely adjusted.

When the inspection apparatus that detects the position coordinates information of the defect stored in the overall control portion 130 and is not shown in the drawing is a defect inspection apparatus using the dark visual field illumination, the rotation angle of the wavelength plate 35 is adjusted in the dark visual field illumination system 300, the laser beam emitted from the laser beam source 30 is reflected by the mirror 38 or 39 to illuminate the reviewing object substrate 100 and the defect of the reviewing object substrate 100 is detected. At this time, scattered light due to the dark visual field illumination from the pattern formed on the reviewing object substrate 100 is cut off by the spatial filter 10 of the detection optical system 350 and only scattered light from the defect reaches the optical detector 15.

Figure 15B:
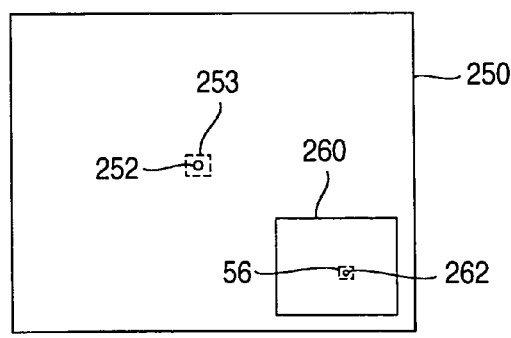
FIG. 15B shows an SEM reviewing screen when a dark visual field detection image is displayed in superposition.

As described above, it is basically not easy for the SEM to review the defect existing in the transparent film of the reviewing object substrate 100. Therefore, the signal of scattered light of the detected defect is processed by the signal processing portion 400 to distinguish the defect 803 on the surface of the transparent film 804 from the defect 802 inside the film, is stored in the overall control portion 130 with the position information of the defect and is fed back at the time of the SEM observation to prevent the result from being regarded as the erroneous judgment of the inspection apparatus. As shown in FIG. 15B, the dark visual field image 260 of the optical microscope acquired by taking the image of the calescence point 56 of the defect at the time of retrieval of the defect is stored in the overall control portion 130 and is displayed with the dark visual field image 260 inside the SEM observation screen 250 at the time of the SEM observation. Furthermore, an index 253 representing the observation position is displayed inside the SEM observation screen while an index 262 is displayed inside the dark visual field image 260. As these indices are moved in synchronism with the moving distance of the XY stage, matching between the dark visual field image and the SEM observation image can be acquired on the real time basis.

As explained above, when the defect is observed through the SEM on the basis of the defect coordinates reviewed by other inspection apparatus, the invention detects and distinguishes with high resolution the defect on the surface of the transparent film formed on the surface of the reviewing object substrate from the defect inside the film, feeds back the defect for the SEM observation and can thus bring easily the defect of the film surface into the visual field. The invention can review in detail the defect of the film surface and can specify the kind of the defect from the features of the defect image. Because parallel display of the SEM image and the dark visual field image and navigation by the indices are employed, the invention can shorten the defect retrieving time when observation is made with eye in the SEM observation.

The invention may be embodied in other forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore to be embraced therein.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A method for reviewing a defect on a sample surface by using an electron microscope, comprising the steps of:

positioning a defect to be reviewed on the sample surface into a visual field of a detection optical system in a vacuum environment inside a vacuum chamber on a basis of position information of the defect acquired in advance by detection with another inspection apparatus;

detecting light scattered from said sample using a detector disposed outside said vacuum chamber, the scattered light being passed through an objective lens disposed inside said vacuum chamber and movable in a height direction of the sample surface independently of the detector so as to obtain a higher numerical aperture for the objective lens as compared with an objective lens disposed outside said vacuum chamber by illuminating said defect positioned inside said visual field with a laser through an inside of a lens barrel of the objective lens by obliquely illuminating said defect from a plurality of directions having mutually different incidence angles so as to conduct a dark field illumination, a position of the objective lens being set based on normal reflected light of the illuminated laser which is detected through the inside of the lens barrel of the objective lens;

processing a signal acquired by detecting said scattered light which is passed through said objective lens disposed inside said vacuum chamber so as to have the higher numerical aperture to distinguish a defect on the surface of said sample from a defect below the surface;

positioning said defect distinguished as existing on the surface of said sample into an observation visual field of the electron microscope inside said vacuum chamber; and reviewing said defect positioned inside said observation visual field by the electron microscope.

2. A method for reviewing a defect on a sample surface by using an electron microscope according to claim 1, further comprising the steps of:

illuminating said defect positioned inside said visual field from a plurality of directions having mutually different incidence angles by sequentially switching the illumination in said step of detecting light;

detecting light scattered from said sample in synchronism with the sequential switching of said illumination; and processing a signal acquired by detecting light scattered from said sample in synchronism with the sequential switching of said illumination to distinguish the defect on a surface of said sample from a defect below the surface in said step of distinguishing the defect on the surface of said sample from the defect below the surface.

3. A method for reviewing a defect on a sample surface by using an electron microscope according to claim 1, further comprising the step of:

correcting the position information of said defect acquired in advance by detection by using the other inspection apparatus on the basis of position information of said detected defect on said sample.

4. A method for reviewing a defect on a sample surface by using an electron microscope according to claim 3, further comprising the step of:

moving said substrate from inside the visual field of said detection optical system into the visual field of said electron microscope in said step of positioning said defect to be observed into the visual field of said detection optical system on the basis of the position information of said defect corrected in said step of correcting the position information of said defect, and setting said defect detected by said detection optical system and distinguished as existing on the surface of said optical transparent film into the visual field of said electron microscope.

5. A method for reviewing a defect on a sample surface by using an electron microscope according to claim 1, further comprising the step of:

reviewing said defect with said electron microscope to acquire an SEM image of said defect, extracting feature quantities of said defect and classifying said defect reviewed in accordance with the feature quantities so extracted, in said step of observing said defect.

6. A defect reviewing apparatus including optical detection means and electron microscope means, comprising:

a vacuum chamber having an inside adapted to be evacuated to a vacuum;

table means disposed inside said vacuum chamber for positioning a defect on a sample surface to be reviewed into a visual field of optical detection means on a basis of position information of a defect detected and acquired in advance by using an other inspection apparatus;

said optical detection means including an illumination portion for obliquely illuminating said defect positioned inside said observation visual field by said table means from a plurality of directions having mutually different incidence angles with a laser through an inside of a lens barrel of the objective lens so as to conduct dark field illumination, a detection portion disposed outside said vacuum chamber for detecting light scattered from said sample caused by the illumination of the illumination portion and passed through an objective lens disposed inside said vacuum chamber and movable in a height direction of the sample surface independently of the detection portion so as to obtain a higher numerical aperture for the objective lens as compared with an objective lens disposed outside said vacuum chamber, and a signal processing portion for processing a signal acquired by the detection of the scattered light which is passed through said objective lens disposed inside said vacuum chamber so as to have the higher numerical aperture and distinguishing a defect on a surface of said sample from a defect below the surface, a position of the objective lens being set based on normal reflected light of the illuminated laser which is detected through the inside of the lens barrel of the objective lens;

table position controlling means for driving said table means and moving and positioning said defect distinguished as existing on the surface of said sample from inside the observation visual field of said optical detection means into the observation visual field of said electron microscope; and electron microscope means for imaging an SEM image of said defect positioned inside the observation visual field by said table position controlling means.

7. A defect reviewing apparatus including optical detection means and electron microscope means according to claim 6, wherein said illumination portion of said optical detection means illuminates said defect positioned inside said observation visual field by said table means from a plurality of directions having mutually different incidence angles while switching said illumination, and said detection portion detects light scattered from said sample illuminated by said illumination portion in synchronism with sequential switching of said illumination.

8. A defect reviewing apparatus including optical detection means and electron microscope means according to claim 6, wherein said signal processing portion of said optical detection means distinguishes a defect on the surface of said sample from a defect below the surface and acquires position information of said defect on the surface of said sample, said table position controlling means corrects position information of a defect detected and acquired in advance by using other inspection apparatus on the basis of the position information of said defect on the surface of said sample acquired by said signal processing portion, drives said table means and moves and positions said defect on the surface of said sample from inside the observation visual field of said optical detection means into the observation visual field of said electron microscope.

9. A defect reviewing apparatus including optical detection means and electron microscope means according to claim 6, wherein said detection portion of said optical detection means further includes a spatial filter which cuts off a diffraction light pattern formed on a pupil plane of said objective lens by light scattered from a repetition pattern formed on said sample by the illumination of said illumination portion.

10. A defect reviewing apparatus including optical detection means and electron microscope means according to claim 6, wherein said detection portion of said optical detection means has an optical detector including an imaging lens and a large number of light reception elements, and an image formed by said imaging lens with light scattered from said sample is detected by said optical detector.

11. A defect reviewing apparatus including optical detection means and electron microscope means according to claim 6, wherein said optical detection means further includes a height detection portion for optically detecting a height of the surface of said sample.

12. A defect reviewing apparatus including optical detection means and electron microscope means according to claim 6, further comprises display means which simultaneously displays both of the image of said defect on the surface of said sample detected by said optical detection means and the SEM image of said defect on the surface of said sample taken by said electron microscope means on a screen of said display means.

13. A method for reviewing a defect on a sample surface by using an electron microscope according to claim 1, wherein a laser beam is irradiated to a sample while a status of polarization of the laser beam is controlled.

14. A method for reviewing a defect on a sample surface by using an electron microscope according to claim 1, wherein the lens barrel, the objective lens, a first mirror which guides the illuminated laser to the sample, and a second mirror which guides the normal reflected light of the illuminated laser to the position detector are moved integral with each other.

15. A defect reviewing apparatus including optical detection means and electron microscope means according to claim 6, further comprising:

a first mirror which guides the illuminated laser to the sample; and a second a second mirror which guides the normal reflected light of the illuminated laser to the position detector;

wherein the lens barrel, the objective lens, the first mirror, and the second mirror are moved integrally with each other.

* * * * *